(12) United States Patent
Angelo et al.

(10) Patent No.: US 6,214,776 B1
(45) Date of Patent: Apr. 10, 2001

(54) HIGH STRESS ELECTRICAL OIL

(75) Inventors: Jacob B. Angelo, Spring, TX (US); Christopher Jeffrey Still Kent, Baton Rouge, LA (US); Frederick Michael Gragg, El Lago, TX (US)

(73) Assignee: Exxon Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/316,660

(22) Filed: May 21, 1999

(51) Int. Cl.$^7$ .................................................. C10M 141/06
(52) U.S. Cl. ............................ 508/281; 508/280; 508/584
(58) Field of Search .................................... 508/281, 280, 508/584

(56) References Cited

U.S. PATENT DOCUMENTS

| | | | |
|---|---|---|---|
| 4,701,273 | * | 10/1987 | Brady et al. . |
| 4,880,551 | * | 11/1989 | Doe . |
| 5,167,847 | * | 12/1992 | Olavesen et al. ..................... 508/110 |
| 5,254,272 | * | 10/1993 | Walters et al. . |
| 5,580,482 | * | 12/1996 | Chasan et al. . |
| 5,849,925 | * | 12/1998 | Karol et al. . |
| 6,046,144 | * | 4/2000 | Karol et al. . |

FOREIGN PATENT DOCUMENTS

| | | | |
|---|---|---|---|
| 0497467 | * | 8/1992 | (EP) . |
| 0499359 | * | 8/1992 | (EP) . |
| 1215001 | * | 12/1970 | (GB) . |
| 9302165 | * | 2/1993 | (WO) . |

* cited by examiner

*Primary Examiner*—Jerry D. Johnson
(74) *Attorney, Agent, or Firm*—Joseph J. Dvorak

(57) ABSTRACT

An oil composition useful as a high stress electrical oil and especially as a transformer load tap changer oil is provided. The composition comprises a major amount of a paraffinic oil having a low viscosity of less than about 20 cSt @ 40° C. and an effective amount of an additive system including at least one hindered phenolic antioxidant and a benzotriazole metal deactivator.

7 Claims, No Drawings

HIGH STRESS ELECTRICAL OIL

FIELD OF THE INVENTION

This invention relates generally to electrical and transformer oils and more particularly to electrical oils suitable for use in electrical devices operating under severe electrical stress such as circuit breakers, switchgear and load tap changers.

BACKGROUND OF THE INVENTION

Present commercial practice is to use conventional naphthenic transformer oils in electrical devices operating under severe stress such as transformer load tap changers. Unfortunately such oils have poor oxidation and chemical stability under severe loading conditions of high current, fast contact switching speeds and arcing. Over time a deposit of carbonaceous material tends to build up on the contacts, distorting the contact surface, insulating the contacts and resulting in overheating of the contact and loss of temper of the contact spring.

Also over time the silver overlay on load top changer contacts may become worn away leaving the copper contact exposed. Exposure of the copper surface to conventional transformer oils tends to catalyze oil oxidation.

One object of the invention is to provide improved transformer load tap changer oils which reduce the build up of deposits on the tap changer contacts and thus extend their in-service life.

Another object of this invention is to provide an oil with improved oxidation stability to minimize the formation of oxidized products in the transformer oil.

A further object of the invention is to provide a load tap changer oil that will provide a film covering any exposed copper surface resulting from wear of contact silver overlay.

Yet another object is to provide an oil that will extend the in-service life of electrical devices such as circuit breakers, switchgear and load tap changers.

These and other objects of the invention will become apparent upon a reading of the description which follows.

SUMMARY OF THE INVENTION

Briefly stated, an oil composition is provided comprising a major amount of a low viscosity paraffinic or naphthenic oil, such as less than about 20 cSt @ 40° C., preferably 5 to 15 cSt @ 40° C. and an effective amount of an additive system which includes:

i) at least one hindered phenol anti-oxidant, and ii) a metal deactivator

The composition is especially useful as an electrical and transformer oil.

DETAILED DESCRIPTION OF THE INVENTION

The composition of the present invention utilizes a major amount of a low viscosity paraffinic oil having a viscosity less than about 20 cSt @ 40° C., preferably 5 to 15 cSt @ 40° C. An example of such an oil is a solvent refined 75N paraffinnic basestock sold by Exxon Corporation, Dallas, Tex.

The composition also utilizes an additive system which includes (i) at least one hindered phenol antioxidant, (ii) metal deactivator.

Typical hindered phenolic antioxidants suitable in the compositions of the present invention may be represented by formula I and formula II:

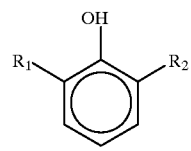

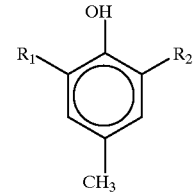

where $R_1$ and $R_2$ may be the same or different alkyl groups, especially branched alkyl groups, containing 3 to about 9 carbon atoms. Preferred phenolic antioxidants include 2,6 di-tert-butylphenol, 2,6 di-tert-butylparacresol and mixtures thereof.

The additive system also includes a metal deactivator such as an alkyl substituted benzotriazole present as a reaction product of the benzotriazole and a diphenyl amine. The preferred metal deactivator is 1,2,3 tolytriazole. This reaction product of the benzotriazole and the diphenyl amine is used in place of the benzotriazole and diphenyl amine as separate components to facilitate blending of the oil, since the benzotriazole typically is a solid and must be dissolved in the oil, whereas the blend of the two is a liquid. A typical benzotriazole diphenyl amine may be represented by the formula III

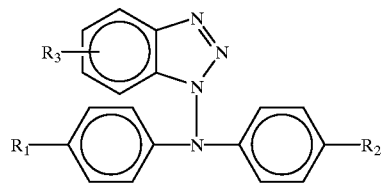

wherein $R_1$ and $R_2$ may be the same or different alkyl groups having from about 3 to about 15 and preferably about 4 to about 9 carbon atoms and $R_3$ is an alkyl group of from 1 to about 15 carbon atoms and preferably 1 carbon atom.

In general, the additive system in the composition is present in a minor but effective amount. For example, the hindered phenol or mixtures thereof typically will comprise from about 0.05 to about 3.0 wt % based on the weight of the paraffmic oil, and preferably 0.5 wt % to 2.0 wt %. The metal deactivator typically will comprise from about 0.01 to about 1.5 wt %, based on the weight of the paraffinic oil, and preferably from about 0.10 to 1.0 wt %.

Finally, the additive system may also include a pour point depressant capable of lowering the pour point to below the lowest temperature expected for the climate in which the tap changer is to be used. This would normally be a temperature of −30° C. to −40° C. A particularly preferred class of pour point depressants is alkylated polystyrenes. The pour point depressant will comprise from about 0.10 to about 1.0 wt %, based on the weight of paraffinic oil and preferably from 0.4 to 0.8 wt %.

Alternatively this low temperature performance can be provided through the use of a base oil having the requisite pour point achieved for example by catalytic dewaxing or solvent dewaxing.

EXAMPLE 1

A transformer load tap changer oil was formulated using as the base oil a Solvent Neutral 75N with a viscosity of 13.4 cSt at 40° C. This Solvent Neutral 75N is commonly referred to as a 75 SSU at 100 °F. paraffinic stock. The formulation contained 2,6 di-tert-butyl phenol, 2,6 di-tert-butyl paracresol, tolyltriazole diphenyl amine and alkylated polystyrene in the amounts shown in Table 1. The formulated oil was tested for oxidation stability using the ASTM D 2440 test. These data for Example 1 are shown in Table 2.

TABLE 1

FORMULATION FOR EXAMPLE 1

| COMPONENT | CONCENTRATION, WT % |
| --- | --- |
| Solvent Neutral 75 | 98.05 |
| Tolyltriazole diphenyl amine | 0.30 |
| 2,6, di-tert-butyl phenol | 0.75 |
| 2,6, di-tert-butyl paracresol | 0.50 |
| Alkylated polystyrene | 0.40 |

A transformer load tap changer oil of the composition as in Table 1 had the physical, chemical and electrical properties set forth in Table 2 determined. The results in Table 2 are compared to ASTM D 3487 specifications for a conventional 60 SSU @ 100° F. naphthenic (Comparative Example 1) electrical oil that is used in load tap changers.

TABLE 2

| DESCRIPTION | ASTM TEST METHOD | EXAMPLE 1 | COMPARATIVE EXAMPLE 1 ASTM D 3487 Type II Oil |
| --- | --- | --- | --- |
| Physical Properties | | | |
| API Gravity, 60/60° F. | | 35.4 | |
| Specific Gravity, 60/60° F. | D1298 | 0.8477 | 0.864–0.878 |
| Viscosity @ 40° C., cSt/SSU | D 88 | 13.26 | 7.4–8.6 |
| Viscosity @ 100° C., cSt/SSU | D 88 | 3.20 | 2.0–2.4 |
| Viscosity @ 100° F., cSt/SSU | D 88 | 14.30 | NA |
| Viscosity @ 210° F., cSt/SSU | D 88 | 3.26 | NA |
| Pour Point, ° C. | D 97 | −33 | −45 max |
| Color, ASTM | D 1500 | L0.5 | 0.5 max |
| Flash Point (COC), ° C. | D 92 | 178 | 146 min |
| Sulfur, wt % | X-ray | 0.026 | 0.20 max |
| Neut Number, mg KOH/g | D 974 | 0.008 | 0.03 max |
| Water by KF, PPM | D 1533 | 25 | 30 max |
| Chemical Properties | | | |
| Corrosive Sulfur | D 1275 | Non-corrosive | Non-corrosive |
| Antioxidant Content, mass % | D2668, D1473 | 1.25 | 0.30 max |
| Oxidation Stability @ | D 2440 | 130° C.[(1)] | 110° C. |
| 72 Hours: | | | |
| Sludge, wt % | | 0.002 | 0.10 max |
| Neutralization Value, mgKOH/g | | 0.028 | 0.30 max |
| 164 Hours: | | | |
| Sludge, wt % | | 0.003 | 0.20 max |
| Neutralization Value, mgKOH/g | | 0.066 | 0.40 max |

TABLE 2-continued

| DESCRIPTION | ASTM TEST METHOD | EXAMPLE 1 | COMPARATIVE EXAMPLE 1 ASTM D 3487 Type II Oil |
| --- | --- | --- | --- |
| 336 Hours: | | | |
| Sludge, wt % | | 0.003 | — |
| Neutralization Value, mgKOH/g | | 0.279 | — |
| 500 Hours: | | | |
| Sludge, wt % | | 0.182 | — |
| Neutralization Value, mgKOH/g | | 1.56 | — |
| Electrical Properties | | | |
| Dielectric Breakdown Voltage @ 60 Hertz, KV | | 56 | 30 min |
| Impulse Breakdown Voltage @ 25° C., KV Needle (negative) - to - sphere (grounded), @ 1-IN Gap | | — | 145 min |
| Power Factor @ 60 Hertz, % | | | |
| 25° C. | | 0.004 | 0.02 max |
| 90° C. | | 0.213 | 0.20 max |
| 100° C. | | 0.253 | 0.30 max |
| Gassing Tendency @ 80° C., μL/min | | — | 0.0 max |
| Static Charge Density, μC/m³ | | 8 | 50 max |

Note: [(1)]Test was modified to increase severity by increasing temperature to 130° C.

What is claimed is:

1. An oil electrical composition comprising:

a major amount of a paraffinic or naphthenic oil having a viscosity less than about 20 cSt @ 40° C.

and, a minor amount of an additive system including:

(i) at least one hindered phenol antioxidant, and (ii) an alkyl substituted benzotriazole diphenyl amine metal deactivator having the formula

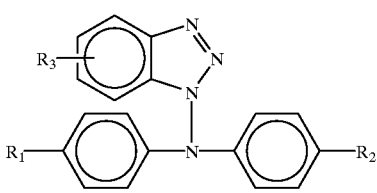

wherein $R_1$ and $R_2$ are the same or different alkyl groups of from about 3 to about 15 carbon atoms, and $R_3$ is an alkyl group of from 1 to about 15 carbon atoms.

2. The composition of claim 1 wherein the hindered phenol antioxidant is selected from phenols and mixtures thereof having the formula

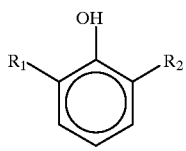

(I)

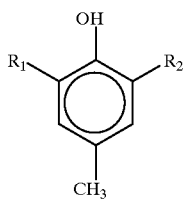

(II)

where $R_1$ and $R_2$ or the same or different alkyl groups having 3 to about 9 carbon atoms.

3. The composition of claim 2 wherein the hindered phenolic antioxidant comprises from about 0.05 to about 3.0 wt % based on the weight of the paraffinic or naphthenic oil.

4. The composition of claim 3 wherein the metal deactivator comprises from about 0.01 to about 1.5 wt % based on the weight of the paraffinic or naphthenic oil.

5. The composition of claim 4 including a pour point depressant in an amount ranging from about 0.10 to about 1.0 wt % based on the weight of paraffinic or naphthenic oil.

6. The composition of claim 5 wherein the paraffinic or naphthenic oil is a dewaxed oil.

7. An electrical oil composition comprising:
   a major amount of a paraffinic or naphthenic oil having a viscosity less than about 20 cSt @ 40° C.; and
   a minor amount of an additive system including:
   (i) a hindered phenol and mixtures thereof antioxidant selected from phenols having the formula

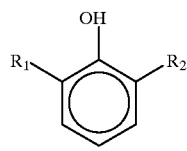

(I)

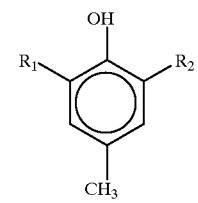

(II)

where $R_1$ and $R_2$ are the same or different branched alkyl groups having 3 to about 9 carbon atoms; and (ii) an alkyl substituted benzotriazole diphenyl amine metal deactivator having the formula

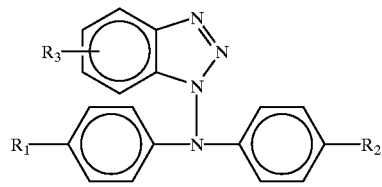

where $R_1$ and $R_2$ are the same or different alkyl groups of from about 3 to about 15 carbon atoms and $R_3$ is an alkyl group of from 1 to about 15 carbon atoms.

* * * * *